US006162634A

United States Patent [19]
Lawler et al.

[11] Patent Number: 6,162,634
[45] Date of Patent: Dec. 19, 2000

[54] ENZYME-PRODUCING STRAIN OF BACILLUS BACTERIA

[75] Inventors: David Lawler; Steven Smith, both of Cheshire, Conn.

[73] Assignee: Roebic Laboratories, Inc., Orange, Conn.

[21] Appl. No.: 09/291,059

[22] Filed: Apr. 14, 1999

[51] Int. Cl.⁷ .............................. A23K 1/00; B09B 3/00; C02F 3/00; C12N 1/00; C12N 1/20

[52] U.S. Cl. .................. 435/252.5; 210/601; 210/610; 210/611; 426/53; 435/252.4; 435/262.5; 435/832; 435/839

[58] Field of Search .................. 435/252.31, 252.4, 435/832, 262.5, 839, 252.5; 210/600, 610, 601, 611; 426/60, 442, 53

[56] References Cited

U.S. PATENT DOCUMENTS

| | | | |
|---|---|---|---|
| 4,288,545 | 9/1981 | Spraker | 435/42 |
| 4,350,770 | 9/1982 | Spraker | 435/253 |
| 4,482,632 | 11/1984 | Spraker | 435/253 |
| 4,655,794 | 4/1987 | Richardson et al. | 51/293 |
| 4,666,719 | 5/1987 | Spiller | 426/18 |
| 4,855,051 | 8/1989 | Insell | 210/601 |
| 4,882,059 | 11/1989 | Wong et al. | 210/606 |
| 4,959,311 | 9/1990 | Shih et al. | 435/68.1 |
| 5,104,801 | 4/1992 | Kilbane, II | 435/282 |
| 5,271,844 | 12/1993 | Chinloy et al. | 210/611 |
| 5,449,619 | 9/1995 | Griffin et al. | 435/264 |
| 5,637,210 | 6/1997 | Vail et al. | 210/150 |
| 5,648,262 | 7/1997 | Damhus et al. | 435/263 |
| 5,869,038 | 2/1999 | Leifert et al. | 424/93.4 |

OTHER PUBLICATIONS

Semco Laboratories, Inc. Product Literature (1995).
Sybron Biochemical Bi–Chem Information (1990).
Chris Hansen Forage Innoculent Products Information (1996).
B.C. Saunders, et al. Peroxidase, pp. 10–12 (London, 1964).
W. Schreiber, Biochem, Biophys. Res. Commun. 63(2), 1975, pp. 509–514.
B.P. Wasserman, J. Food Sci. 49, 1984, pp. 536–538.
A. Ben Aziz, Phytochemistry, 10 1971, pp. 1445–1452.
Mari et al., "Postharvest biol. control of grey mould on fresh–market . . . ", Crop. Protection, vol. 15, No. 8, 699–705, Dec. 1996.
Da Luz et al., "Seed microbioliz. for control of Fusarium sp. in cereals". Phytopathology, vol. 87, No. 6 (1997).
Qiu et al., "Primary microbial populations in active sludge processing. for wastewater treatment in printing and dyeing industry". Fazhou Daxue Xuebao, vol. 24, No. 5 (1997) (with English abstract and translation of one page.).
Gustafson Kodiak Concentrate Biological Fungicide Information (1996).
ATCC Bacteria and Bacteriophages, Nineteenth ed., 1996, pp. on Family Bacillaceae and Tables 13.4 and 13.6.
Sneath, Peter H.A.; Endospore–forming Gram–Positive Rods and Cocci; Bergey's Manual of Systematic Bacteriology, vol. 2, Section 13; pp. 1104–1139.
1999 Official Publication of the Association of American Feed Control Offiicials, (AAFCO), p. 221.
DFM Products; Product Information; A Publication of CHR, Hansen BioSystems; pp. 1–2; Apr. 1996.
DFM Products, "Contains a source of live, naturally occurring microorganisms"; CHR Hansen BioSystems; pp. 1–2; Apr. 1996.
Sportzyme Ultrabase 2; "Liquid Base Ingredient Containing a Bacterial Spore System"; Semco Laboratories, Inc.; pp. 1–2.
Sportzyme BBC; "A Dry Blend of Purified Bacterial Spores"; Semco Laboratories, Inc. pp. 1–2.
Microcheck, The Validation Consultant, vol. 3, No. 3, Mar. 1996.

*Primary Examiner*—Leon B. Lankford, Jr.
*Assistant Examiner*—Deborah K. Ware
*Attorney, Agent, or Firm*—Covington & Burling

[57] ABSTRACT

This invention presents a newly discovered, novel strain of Bacillus bacteria that produces lipase enzymes for the degradation of oleaginous materials such as fats, greases and cooking oils, protease enzymes to degrade proteins and amylases to break down starch. This novel strain and the enzymes produced thereby have a number of applications, including wastewater treatments, agricultural uses, laundry and dish detergents, drain cleaners and spot removers, among others.

9 Claims, 4 Drawing Sheets

```
ID:     25744      ROE RLM-007Aa                           DATE OF RUN: 18-FEB-98  06:15:11
BOTTLE: 34         SAMPLE     [AEROBE]
```

| RT | AREA | AR/HT | RESPON | ECL | NAME | % | COMMENT 1 | COMMENT 2 |
|---|---|---|---|---|---|---|---|---|
| 1.771 | 369840640 | 0.035 | · · · | 6.999 | SOLVENT PEAK | | < MIN RT | |
| 5.546 | 920 | 0.038 | 1.053 | 12.612 | 13:0 ISO | 0.61 | ECL DEVIATES -0.000 | REFERENCE 0.007 |
| 6.818 | 1112 | 0.059 | 1.010 | 13.619 | 14:0 ISO | 0.71 | ECL DEVIATES 0.001 | REFERENCE 0.007 |
| 7.328 | 2016 | 0.043 | 0.996 | 13.998 | 14:0 | 1.26 | ECL DEVIATES -0.002 | REFERENCE 0.004 |
| 8.274 | 61448 | 0.044 | 0.975 | 14.622 | 15:0 ISO | 37.74 | ECL DEVIATES 0.001 | REFERENCE 0.006 |
| 8.410 | 52528 | 0.044 | 0.972 | 14.712 | 15:0 ANTEISO | 32.17 | ECL DEVIATES 0.001 | REFERENCE 0.006 |
| 8.847 | 1104 | 0.051 | 0.963 | 14.999 | 15:0 | 0.67 | ECL DEVIATES -0.001 | REFERENCE 0.004 |
| 9.875 | 1368 | 0.048 | 0.946 | 15.626 | 16:0 ISO | 0.82 | ECL DEVIATES 0.000 | REFERENCE 0.005 |
| 10.092 | 5440 | 0.048 | 0.943 | 15.758 | 16:1 w11c | 3.23 | ECL DEVIATES 0.001 | |
| 10.487 | 10512 | 0.049 | 0.937 | 15.999 | 16:0 | 6.21 | ECL DEVIATES -0.001 | REFERNCE 0.004 |
| 11.154 | 4304 | 0.052 | 0.928 | 16.389 | ISO 17:1 w10c | 2.52 | ECL DEVIATES 0.002 | |
| 11.309 | 1248 | 0.058 | 0.927 | 16.480 | SUM IN FEATURE 5 | 0.73 | ECL DEVIATES 0.004 | 17:1 ISO I/ANTEI B |
| 11.565 | 15232 | 0.050 | 0.924 | 16.630 | 17:0 ISO | 8.86 | ECL DEVIATES 0.001 | REFERENCE 0.005 |
| 11.723 | 7704 | 0.050 | 0.922 | 16.722 | 17:0 ANTEISO | 4.47 | ECL DEVIATES -0.000 | REFERENCE 0.004 |
| 14.982 | 344 | 0.021 | · · · | 18.602 | | | | |
| ****** | 1248 | · · · | · · · | · · · | SUMMED FEATURE 5 | 0.73 | 17:1 ISO I/ANTEI B | 17:1 ANTEISO B/i I |

| SOLVENT AR | TOTAL AREA | NAMED AREA | % NAMED | TOTAL AMNT | NBR REF | ECL DEVIATION | REF ECL SHIFT |
|---|---|---|---|---|---|---|---|
| 369840640 | 165280 | 164936 | 99.79 | 158691 | 10 | 0.001 | 0.005 |

```
TSBA [REV 3.90]  BACILLUS . . . . . . . . . . . . . . . . . . . . 0.475
                 B. SUBTILIS* . . . . . . . . . . . . . . . . . . 0.475
                 B. AMYLOLIQUEFACIENS . . . . . . . . . . . 0.460  (BACILLUS SUBTILIS GROUP)
                 B. PUMILUS . . . . . . . . . . . . . . . . . . 0.436  (OTHER THAN TYPE STRAIN)
                   B. P. GC SUBGROUP B* . . . . . . . . . . 0.436  (OTHER THAN TYPE STRAIN)
                   B. P. GC SUBGROUP A . . . . . . . . . . . 0.282  (SIMILAR TO TYPE STRAIN)
                 PAENIBACILLUS . . . . . . . . . . . . . . . . . 0.255  (BACILLUS)
                   P. MACERANS . . . . . . . . . . . . . . . . 0.255  (BACILLUS)
                     P. M. GC SUBGROUP A . . . . . . . . . . . 0.255  (BACILLUS)
```

```
COMPARISON WITH TSBA [REV 3.90]: BACILLUS-SUBTILIS*                                 DISTANCE:4.335
               0   5  10  15  20  25  30  35  40  45  50  55  60  65  70  75  80  85  90  95  100
13:0 ISO . . . . . . +X- .
14:0 ISO . . . . . . . -+- .
14:0 . . . . . . . . . +X- .
15:0 ISO . . . . . . .              -----------+----------- . X .
15:0 ANTEISO . . . . .                            . X -----+-----
15:0 . . . . . . . . . +X- .
16:0 ISO . . . . . . . -X-+-- .
16:1 w11c . . . . . . . -+X .
16:0 . . . . . . . . . --+-X .
ISO 17:1 w10c . . . . . -+X- .
17:0 ISO . . . . . . .      . -X-+----
17:0 ANTEISO . . . . . .  X.    ----+-----
SUMMED FEATURE 5 . . -+- .
```

Figure 4

ENZYME-PRODUCING STRAIN OF BACILLUS BACTERIA

FIELD OF THE INVENTION

This invention consists of a newly discovered, novel strain of Bacillus bacteria which produce multiple useful enzymes. The novel bacterium and the enzymes it produces have a number of applications, including wastewater treatment, agricultural uses, laundry and dish detergents, drain cleaners and spot removers, among others. In particular, the Bacillus strain of the present invention produces lipase enzymes for the degradation of oleaginous materials such as fats, greases and cooking oils, as well as protease enzymes to degrade proteins and amylases to break down starch.

BACKGROUND OF THE INVENTION

The use of bioaugmentation, i.e., the addition of non-indigenous bacteria to a wastewater to effect more complete treatment and purification of the water, is becoming more and more necessary as municipal sewage plants age and demands brought on by increasing loads require improvements in efficiency. Bioaugmentation, also called bacterial augmentation, can be beneficial in a number of applications. For example, bacterial augmentation can improve the quality and efficiency of treatment of municipal wastewater, food processing wastewater, and residential wastewater, especially in on-site disposal systems such as septic tanks and cesspools, pretreatment of wastewater that might contain high levels of oleaginous matter, and treatment of pipes, traps, plumbing systems and grease traps.

Enzyme-producing bacteria also have agriculture uses as silage inoculant products to improve efficiency and production of livestock that consume the treated silage. Certain bacteria, called Direct Fed Microbials, may also be added to livestock feeds to increase food digestion and utilization. Currently both *Bacillus subtilis* and *Bacillus pumilus* have were found by the Food and Drug Administration to present no safety concerns when used in direct-fed microbial products, as published by the Association of American Feed Control Officials (AAFCO). 1999 Official Publication of the Association of American Feed Control Officials, p. 221. In addition, advances in bioengineering have demonstrated that a genetic characteristic from one species, including bacteria, can be inserted into the DNA of another species. One important example is the insertion of the gene responsible for the production of an insecticidal protein from *Bacillus thuringiensis* into the DNA of corn seeds. The resultant corn plant is able to produce a protein which kills insect pests such as the corn rootworm, thereby producing healthier corn plants and improved per-acre yields.

SUMMARY OF THE INVENTION

The object of this invention therefore is to provide a novel strain of bacteria which produces specific types of useful enzymes.

It is a further object of the present invention to provide a novel strain of bacteria that produces lipase enzymes to degrade fat, proteases to degrade proteins, and amylases to degrade starch.

It is another object of the present invention to provide a novel multiple-enzyme-producing bacterial strain that is useful for wastewater applications to enhance degradation of the organic components of the wastewater and therefore improve the quality and efficiency of the water treatment process.

It is yet a further object of the present invention to provide a novel multiple-enzyme-producing strain of bacteria for use in agricultural applications, including as Direct Fed Microbials in livestock feed formulations, as silage innoculants and to treat livestock manure.

It is a still further object to provide novel bacteria and/or enzymes produced from such bacteria for use as detergents, and to provide enzymes to use as stain removers or in food processing applications.

The present invention provides a novel stain of Bacillus bacteria that produces lipases to degrade fat, proteases to degrade proteins, and amylases to degrade starch. The novel strain disclosed and claimed in the present application is one of eight novel strains invented by the present inventors. For completeness of description, the specification will describe all eight strains, but only the Bacillus strain designated as ATCC 202138 is claimed in the present application. The eight novel strains of Bacillus bacteria have all been deposited with the American Type Culture Collection ("ATCC"), 10801 University Blvd., Manassas, Va., 20110–2209, U.S.A., on Jun. 5, 1998, under the rules of the Budapest Treaty and are designated as follows:

| Species | Strain | ATCC Number |
|---|---|---|
| Bacillus pumilus | RLM-002 | ATCC 202136 |
| Bacillus subtilis | RLM-007Aa | ATCC 202138 |
| Bacillus amyloliquefaciens | RLM-007Ab | ATCC 202134 |
| Bacillus macerans | RLM-007C | ATCC 202132 |
| Bacillus subtilis | RLM-011 | ATCC 202137 |
| Bacillus subtilis | RLM-012A | ATCC 202139 |
| Bacillus amyloliquefaciens | RLM-012B | ATCC 202133 |
| Bacillus macerans | RLM-013C | ATCC 202135 |

The species of each of these Bacillus bacterial strains were determined using the Fatty Acid Methyl Ester (FAME) Analysis method performed by Microcheck, Inc., of Northfields, Vermont using Trypticase Soy Broth Agar ("TSBA") version 3.9 at 28.0 C of Microcheck's database.

The eight novel Bacillus strains have a variety of potential uses, including treatment of wastewater, such as municipal, food processing, and residential wastewater; pretreatment of wastewater that might contain high levels of oleaginous matter; treatment of on site sewage disposal systems, such as septic tanks and cesspools; agricultural uses, including livestock manure waste management or as Direct Fed Microbials for use in livestock feeds to increase food digestion and utilization; and for treatment of pipes, traps, plumbing systems and grease traps.

BRIEF DESCRIPTION OF THE DRAWINGS

FIG. 4 shows the data generated as a result of the Fatty Acid Methyl Ester (FAME) Analysis method performed by Microcheck, Inc., of Northfields, Vt. using TSBA version 3.9 at 28.0 C of Microcheck's database, which was used to determine the species of *Bacillus subtilis* ATCC 202138.

DETAILED DESCRIPTION OF THE INVENTION

Figure 1:
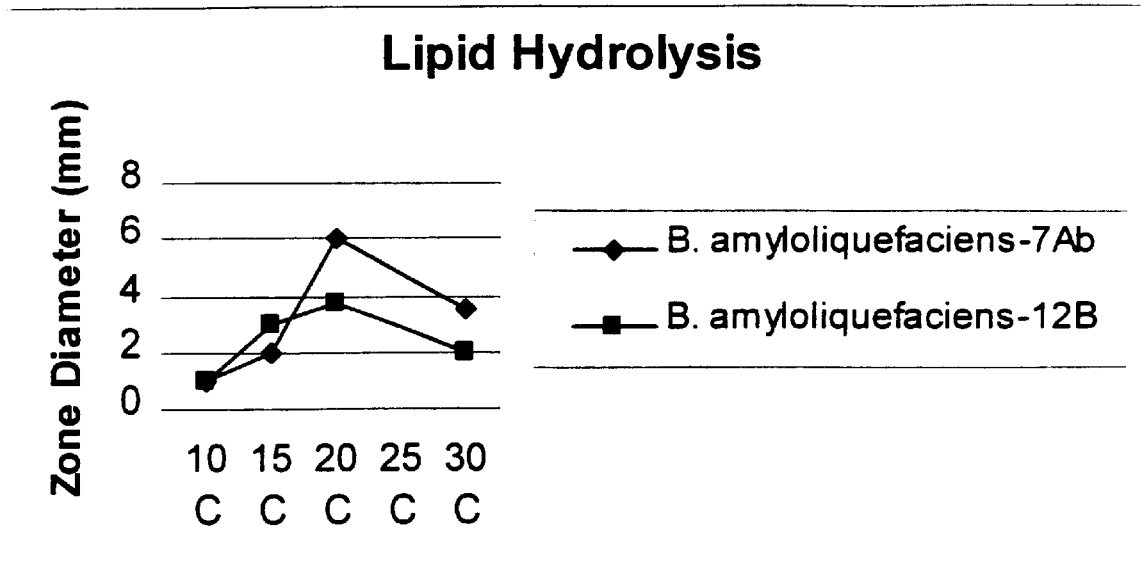
FIG. 1 charts the production of lipase enzymes at various points within a temperature range by *Bacillus amyloliquefaciens* strains RLM-007Ab, ATCC 202134 and RLM-012B, ATCC 202133.

The eight newly discovered strains of Bacillus bacteria were isolated from soil using standard microbiological methods. These strains were isolated using a method which was adapted from Bergey's Manual of Systematic Bacteriology, Vol. 2, pages 1104–1139. The procedure used was selective for the genus Bacillus because of this genus' ability to survive the pasteurization process by producing spores that are resistant to temperatures reached during the pasteurization process. In the procedure, approximately one gram of soil from the vicinity of Seattle, Wash., was added to 300 ml of Tryptic Soy Broth (Difco). This mixture was then pasteurized by heating to 70 C for 10 minutes. The flask was then incubated for 48 hours at 30 C. The culture was struck onto (TSA) Tryptic Soy Agar (Difco) plates at the beginning of the incubation period, following 24 hours of incubation, and at the end of the 48 hours of incubation. These plates were then incubated aerobically at 30 C and examined for their bacterial growth. Bacterial colonies were picked and serially transferred onto TSA plates approximately every 24 to 48 hours until stable bacterial colonies could be isolated.

Taxonomic determination was accomplished via colonial morphology, cellular morphology, Gram stain, biochemical tests, and Fatty Acid Methyl Ester (FAME) Analysis performed by Microcheck, Inc., of Northfields, Vt. using TSBA version 3.9 at 28.0 C. of Microcheck's database.

All eight strains of the of Bacillus bacteria of the present invention are Gram positive rod shaped bacteria that grow under aerobic conditions. As is typical of the genus, they bear spores that germinate to vegetative reproducing cells.

The newly discovered Bacillus strains of the present invention are presented in Table I. The Roebic Laboratories Microbe (RLM) number is given with the species identification as provided by FAME Analysis method performed by Microcheck, Inc., of Northfields, Vt. using TSBA version 3.9 at 28.0 C of Microcheck's database.

Also, the right column provides the similarity indices/ standard deviations (SI/SD).

TABLE I

| Reference | Species Identification | SI/SD |
|---|---|---|
| RLM-002 | *Bacillus pumilus* GC subgroup B | 0.628 |
| RLM-007Aa | *Bacillus subtilis* | 0.475 |
| RLM-007Ab | *Bacillus amyloliquefaciens* | 0.608 |
| RLM-007C | *Paenibacillus macerans* GC subgroup A | 0.729 |
| RLM-011 | *Bacillus subtilis* | 0.519 |
| RLM-012A | *Bacillus subtilis* | 0.435 |
| RLM-012B | *Bacillus amyloliquefaciens* | 0.593 |
| RLM-013C | *Paenibacillus macerans* GC subgroup A | 0.415 |

In order to more fully describe each Bacillus strain, additional biochemical tests were performed to demonstrate the ability to utilize various carbohydrates as nutrient sources, and to use urea and citrate as sources of assimilable carbon. The results are presented in Table II.

TABLE II

CARBOHYDRATE UTILIZATION

| | Strain RLM- | | | | | | | |
|---|---|---|---|---|---|---|---|---|
| Carbohydrates Tested | 002 | 007Aa | 007Ab | 007C | 011 | 012A | 012B | 013C |
| Adonitol | − | − | − | − | − | − | − | − |
| Arabinose | − | − | − | − | + | − | − | − |
| Dulcitol | − | − | − | − | − | − | − | − |
| Glucose | − | + | + | + | + | + | + | + |
| Lactose | − | − | − | − | − | − | − | − |
| Maltose | − | − | − | − | − | − | − | − |
| Mannitol | − | − | + | − | + | − | + | + |
| Sorbitol | − | − | − | + | + | − | − | − |
| Sucrose | + | + | + | + | − | − | + | − |
| Xylose | − | − | − | − | − | − | − | − |
| Carbon Sources Tested | | | | | | | | |
| Urea | − | + | + | + | + | + | + | + |
| Citrate | − | − | − | + | + | − | + | + |

Results from either Becton Dickenson Enterotube II or Oxi/Ferm Tube II at 48 hours at 34 C. These tests were conducted following the manufacturer's instructions and were inoculated with 24 hour Tryptic Soy Agar ("TSA") colonies.

All eight Bacillus strains execept Strain RLM-002 (ATCC 202136) were able to reduce nitrate to nitrite, which is a useful characteristic for the treatment of wastewater where dissolved oxygen levels are low, but nitrate levels are high. This would include on-site sewage disposal systems such as septic tanks and cesspools.

To further identify the specific capabilities of each Bacillus strain, tests were conducted using Tryptic Soy Broth (Difco) ("TSB") to determine the minimum and maximum temperature at which each would grow. The test was conducted using test tubes of TSB incubated at the indicated temperature for 14 days. The results are presented in Table III.

TABLE III

GROWTH TEMPERATURE RANGE

| Strain | 10C | 15C | 40C | 45C | 50C |
|---|---|---|---|---|---|
| RLM-002 *B. pumilus* ATCC 202136 | + | + | + | + | + |
| RLM-007Aa *B. subtilis* ATCC 202138 | + | + | + | + | − |
| RLM-007Ab *B. amyloliquefaciens* | − | + | + | + | − |

TABLE III-continued

GROWTH TEMPERATURE RANGE

| Strain | 10C | 15C | 40C | 45C | 50C |
|---|---|---|---|---|---|
| ATCC 202134 | | | | | |
| RLM-007C B. macerans ATCC 202132 | − | + | + | + | − |
| RLM-011 B. subtilis ATCC 202137 | + | + | + | + | + |
| RLM-012A B. subtilis ATCC 202139 | − | + | + | + | − |
| RLM-012B B. amyloliquefaciens ATCC 202133 | − | + | + | + | − |
| RLM-013C B. macerans ATCC 202135 | − | + | + | + | − |

The fact that all eight Bacillus strains were able to grow at 15 C is particularly useful for wastewater treatment and agricultural applications. Also, two strains of *Bacillus subtilis*, RLM-007Aa and RLM-011, and *Bacillus pumilus* RLM-002 were able to grow at 10 C. The latter strain, along with *Bacillus subtilis* RLM-011, was able to grow at 50 C as well. These two organisms exhibited the widest temperature range within the group of eight strains. Growth over such a wide temperature range significantly expands the areas of usefulness of these novel bacteria to include many applications in the environment.

Table IV identifies the useful enzymes produced by the newly discovered eight Bacillus strains.

TABLE IV

USEFUL ENZYMES PRODUCED

| Strain | Amylase | Lipase | Proteases Gelatin | Casein |
|---|---|---|---|---|
| RLM-002 B. pumilus ATCC 202136 | − | + | + | + |
| RLM-007Aa B. subtilis ATCC 202138 | + | + | + | + |
| RLM-007Ab B. amyloliquefaciens ATCC 202134 | + | + | + | + |
| RLM-007C B. macerans ATCC 202132 | − | + | + | − |
| RLM-011 B. subtilis ATCC 202137 | + | + | + | + |
| RLM-012A B. subtilis ATCC 202139 | + | + | + | + |
| RLM-012B B. amyloliquefaciens ATCC 202133 | + | + | + | + |
| RLM-013C B. macerans ATCC 202135 | + | + | + | + |

EXAMPLE 1

The production of amylase enzymes by bacteria is a useful characteristic with many applications including wastewater treatment and food processing methods. The production of amylase enzymes by the novel strains of the present invention was determined through the use of Bacto Starch Agar (Difco). Simple streaks were used as well as disk zone hydrolysis. Bacto Starch Agar consists of Bacto Beef Extract (3 g/l), soluble starch (10 g/l), and Bacto Agar (12 g/l). To prepare starch agar plates, 25 g/l of Bacto Starch Agar was suspended in de-ionized water. The water was heated so that the starch dissolved completely. The aqueous starch solution was then sterilized for 15 minutes at 120 C and allowed to cool. The media was then poured into plates and allowed to solidify and dry overnight.

For the streak test, a sterile platinum inoculating needle was used to streak a pure strain onto an individual starch agar plate. The plates were then incubated at 30 C. At 24 hours, the plates were flooded with Gram's Iodine solution. This procedure was repeated at 48 hours. A positive result was indicated by a yellow zone surrounding the bacterial growth. If the starch had not been hydrolyzed, then the agar would appear as a very dark purple.

For the disk zone hydrolysis test, sterile paper disks were applied to the surface of dry starch agar plates and were then soaked with a 24-hour pure culture. These plates were then incubated for 24 hours and then flooded with Gram's Iodine solution. This test was also repeated following 48-hour incubation. A positive result was indicated by a yellow zone surrounding the disk.

Table V is a summary of amylase production by the bacteria strains of the present invention.

TABLE V

RESULTS OF AMYLASE TESTING

| Streak Test at 48 Hours | | Disk Zone Hydrolysis Test at 48 Hours | | |
|---|---|---|---|---|
| Strain | +/− | Strain | +/− | Zone (mm)* |
| RLM-002 | − | RLM-002 | − | 0 |
| RLM-007Aa | + | RLM-007Aa | + | 2 |
| RLM-007Ab | + | RLM-007Ab | + | 2 |
| RLM-007C | − | RLM-007C | − | 0 |
| RLM-011 | + | RLM-011 | + | 2.5 |
| RLM-012A | + | RLM-012A | + | 1 |
| RLM-012B | + | RLM-012B | + | 1 |
| RLM-013C | + | RLM-013C | + | 1.5 |

*Measurement was made from the edge of the colony or paper disk to the edge of the zone of hydrolysis.

The data indicate that all strains except RLM-002 and RLM-007C produced amylase enzyme. *Bacillus subtilis* RLM-011 produced the largest zones and presumably the most enzyme.

EXAMPLE 2

The production by bacteria of proteases, or protein degrading enzymes, is also a valuable trait with many applications. The commercial use of such bacteria in wastewater treatment, food processing and laundry detergents presents a substantial commercial market for these bacteria and the enzymes they produce.

The eight novel discovered Bacillus strains were tested with two proteinaceous materials, casein and gelatin, and all strains displayed varying abilities to degrade these proteins. The production of protease enzymes was determined through the analysis of casein hydrolysis and nutrient gelatin liquefaction. Bacto Nutrient Gelatin (Difco) consists of Bacto Beef Extract (3 g/l), Bacto Peptone (5 g/l), and Bacto Gelatin (120 g/l). To prepare Nutrient Gelatin tubes, 128 grams of Bacto Nutrient Gelatin was suspended in 1 liter of de-ionized water. The water was heated so that the gelatin dissolved completely and the aqueous mixture was distributed by 15 milliliter aliquots into test tubes. The tubes were sterilized in the autoclave for 15 minutes at 121 C, and were then allow to cool and solidify. An isolated colony from a TSA plate was touched with a sterile inoculating needle and the needle was stabbed down through the Nutrient Gelatin Agar. The tubes were then incubated for 4 days at 37 C. After the incubation period, the tubes were removed and allowed to cool. A positive result is indicated if any of the gelatin remains liquefied and does not re-solidify.

Casein hydrolysis was tested for both through Bushnell-Haas-Casein ("BHC") plates and then through disk zone analysis on TSA-Casein plates.

Bushnell Haas media is available for purchase pre-made (from Difco Laboratories or a local distributor). It consists of magnesium sulfate (0.2 g/l), calcium chloride (0.02 g/l), monopotassium phosphate (1 g/l), dipotassium phosphate (1 g/l), ammonium nitrate (1 g/l), and ferric chloride (0.05 g/l). Casein, technical grade, and Agar are both available from Difco.

To prepare the Bushnell-Haas-Casein agar plates, 3.25 g/l Bushnell Haas medium was dissolved in 1 liter de-ionized water. To the aqueous mixture, 20 g/l Casein and 20 g/l agar were added sequentially. The mixture was heated so all solutes dissolved completely and was then sterilized at 120 C for 15 minutes. The agar was allowed to cool, poured into plates and allowed to solidify. The plates so prepared were inoculated by touching a sterile inoculating needle to an isolated colony on a TSA plate, and streaking the needle once across the surface of the BHC a gar plate. The streaked plates were incubated for 48 hours at 30 C, and then held at room temperature for two additional days. A positive result was indicated by a clearing of the casein.

TSA-Casein Agar plates were prepared using Difco TSA to which 20 g/l Casein, techyical grade, was added. TSA consists of Bacto Tryptone (15 g/l), Bacto Soytone (5 g/l), Sodium Chloride (5 g/l), and Bacto Agar (15 g/l). To prepare TSA-Casein plates, 40 g/l TSA was suspended in 1 liter of de-ionized water, and twenty grams of Casein was then added. The aqueous mixture was heated so that the solutes dissolve completely, and then sterilized at 120 C for 15 minutes. The mixture was allowed to cool, was poured into plates, and was allowed to solidify and dry overnight. In the center of the each agar plate, a paper disk was placed which was then soaked with a few drops of a 24-hour TSB pure culture of the test organism. The plates were then incubated and examined periodically. A positive result showed clearing of the casein from around the disk within 48 hours.

The following is a summary of protease production as determined by casein hydrolysis (Table VI) and gelatin liquefaction (Table VII).

TABLE VI

RESULTS OF CASEIN HYDROLYSIS TESTING

| BH-Casein Streak Test | | TSA-Casein Disk Zone Hydrolysis Test at 48 Hrs. | | |
|---|---|---|---|---|
| Strain | +/− | Strain | +/− | Zone (mm)* |
| RLM-002 | − | RLM-002 | + | 2 |
| RLM-007Aa | + | RLM-007Aa | + | 1–2 |
| RLM-007Ab | − | RLM-007Ab | + | 1–2 |
| RLM-007C | − | RLM-007C | − | 0 |
| RLM-011 | + | RLM-011 | + | 3–5 |
| RLM-012A | + | RLM-012A | + | 3 |
| RLM-012B | + | RLM-012B | + | 3–4 |
| RLM-013C | + | RLM-013C | + | 3–4 |

TABLE VII

RESULTS OF NUTRIENT GELATIN TESTING

| Strain | Day 2 (48 Hrs.) | Day 4 (96 Hrs.) |
|---|---|---|
| RLM-002 | − | + |
| RLM-007Aa | − | + |
| RLM-007Ab | − | + |
| RLM-007C | − | + |
| RLM-011 | + | + |
| RLM-012A | − | + |
| RLM-012B | + | + |
| RLM-013C | − | + |

EXAMPLE 3

The production of lipase, or fat splitting enzyme(s), by the eight novel Bacillus strains of the present invention is an important characteristic that has significant commercial applications.

All enzymes perform under a range of conditions, most having a maximum level of activity at a given, sometimes narrow, temperature range. Lipolytic activity therefore was tested at several temperatures to demonstrate the active range of the lipase produced as well as the temperature at which it has optimal activity. The test for lipase production utilized Bacto Spirit Blue Agar with Bacto Lipase Reagent (Difco), which is a widely-accepted medium for detecting lipolytic microorganisms. According to its label, the formula for Spirit Blue Agar comprises Bacto Tryptone (10 g/l), Bacto Yeast Extract (5 g/l), Bacto Agar (20 g/l), and Spirit Blue (0.15 g/l). This medium can be purchased already prepared (from Difco Laboratories or a local distributor), or may be prepared as follows: Thirty-five grams of dried medium is suspended in 1 liter of distilled or de-ionized water and the aqueous mixture is heated to boiling so that the solutes are dissolved completely. The solution is then sterilized in an autoclave for 15 minutes at 15 pounds of pressure and 121 C. It is cooled to 50–55 C, and 30 ml of Bacto Lipase Reagent is added aseptically and mixed thoroughly. The desired amount is poured into a 120 millimeter (Falcon 1020) disposable petri dish. The inventors are not aware of the formulation for the lipase reagent, but the reagent can be purchased from Difco.

Spirit Blue Agar with Lipase Reagent plates (SBLP) were held at room temperature overnight in order to both solidify and to dry the surface of the agar. Lipase enzymatic activity was tested by simple bacterial streaking, incubation, and quantitative measuring of the zones of clearing. To streak a plate, a sterile platinum inoculating loop was touched to an isolated colony grown on TSA for a minimum of 48 hours. The loop was then carefully struck twice back and forth across the surface of an SBLP. Following incubation, this procedure yields a continuous and luxuriant growth of bacteria which bifurcates the SBLP plate and allows for the activity of lipase enzymes to be observed over a wide time frame. Plates initially were incubated at about 30 C for 24 hours, zones of clearing were measured, and the plates were then held at room temperature for approximately 7 days during which time additional measurements and observations were made. In evaluating lipolytic activity, simple streaks were used as well as measurements of zones of clearing.

This streak procedure was carried out again at various incubation temperatures which were kept constant throughout the 7 day test in order to elucidate the particular strain's enzymatic activity curves over a wider temperature range. Each strain's lipolytic activity was tested at 10 C, 15 C, 20 C, and 30 C. A positive lipolytic result was indicated by a clearing in the agar medium's opacity immediately surrounding the bacterial growth. The larger this zone of clearing is, the greater the lipase activity for the bacterial strain. Color change in the medium is not fully indicative of lipolytic activity.

The results of this testing are presented on Table VIII.

TABLE VIII

RESULTS OF LIPASE TESTING: ZONES OF CLEARING (mm) ON DAY 7 AT GIVEN TEMPERATURE RANGES (Streak Tests)

| Strain | Incubation Temperature- | | | |
| --- | --- | --- | --- | --- |
|  | 10C | 15C | 20C | 30C |
| RLM-002 | 1 | 3 | 4 | 5 |
| RLM-007Aa | 1 | 2–3 | 2 | 2–3 |
| RLM-007Ab | 1 | 2 | 6 | 3–4 |
| RLM-007C | 1 | 3 | 6.5 | 6 |
| RLM-011 | 1 | 3 | 4 | 7 |
| RLM-012A | 1 | 3 | 5 | 7 |
| RLM-012B | <1 | 3 | 3.5–4 | 2 |
| RLM-013C | 1.5 | 2–3 | 2–3 | 5–7 |

Figure 2:
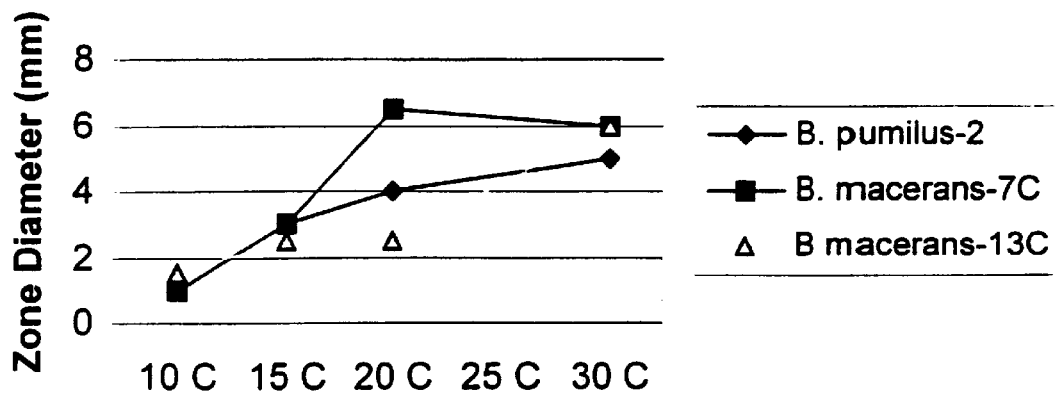
FIG. 2 charts the production of lipase enzymes at various points within a temperature range by *Bacillus macerans* RLM-013C, ATCC 202135 and RLM-007C, ATCC 202132, and *Bacillus pumilus* RLM-002, ATCC 202136.
Figure 3:
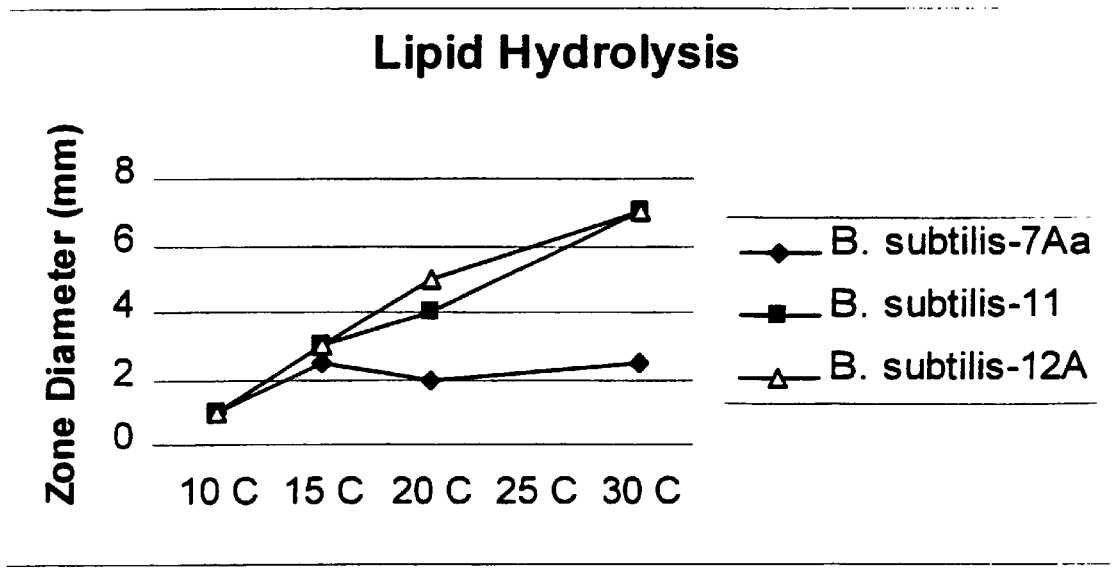
FIG. 3 charts the production of lipase enzymes at various points within a temperature range by *Bacillus subtilis* RLM-011, ATCC 202137, RLM-012A, ATCC 202139, and RLM-007Aa, ATCC 202138.

The data in Table VIII, which are also represented in graph form in FIGS. 1, 2, and 3, clearly demonstrates the production of lipase enzymes capable of splitting fats, grease, oils or other oleaginous materials (lipid hydrolysis). The figures compare the relationship between temperature and lipase enzyme production among the Bacillus strains grouped by species.

While it is generally recognized that bacterial metabolism increases with temperature as it approaches an optimum, FIG. 1 clearly demonstrates that the two *Bacillus amyloliquefaciens* strains RLM-007Ab, ATCC 202134 and RLM-012B, ATCC 202133 produced more lipase activity at 20 C than at 30 C. This characteristic easily positions these strains as the bacteria of choice for use in lower temperature environments such as wastewater treatment or food processing waste treatment in holding tanks or lagoons. It is expected that this characteristic would provide to a treatment product containing one or both of these microbes an advantage over a competitive product that did not perform as well at that temperature.

The bacteria represented on FIG. 2 demonstrate a different pattern of lipase activity. *Bacillus macerans* RLM-013C, ATCC 202135 produced significantly more lipolytic activity at 30 C than at 20 C. The other strain of *Bacillus macerans*, RLM-007C, ATCC 202132, behaved quite differently, exhibiting a dramatic increase in activity from 15 C to its peak at 20 C, which dropped off slightly as the temperature increased to 30 C. The *Bacillus pumilus* RLM-002, ATCC 202136 generally demonstrated increased activity with increasing temperature to a maximum of lipolytic activity at 30 C.

The three strains of *Bacillus subtilis* represented in FIG. 3 displayed a third pattern of activity. Two strains, RLM-011, ATCC 202137, and RLM-012A, ATCC 202139, both produced more lipolytic activity as the temperature increased, but strain RLM-007Aa, ATCC 202138, showed no such increase. Its lipase activity was considerably lower overall, and reached its peak at 15 C.

These varying patterns of lipolytic activity among the Bacillus strains provide the basis for combinations of two or more strains for various applications in which temperature is a factor. Such information is also useful for the mass production of the strains in "fermentors," which are large culture vessels for preparing or "fermenting" batches of bacteria, yeasts, molds, etc. Regardless of whether the bacteria are fermented to be sold as whole cultures, spore concentrates, or if the enzymes were to be harvested and purified for specific market uses, temperature differences play a key role in the selection of strains for particular applications.

All eight Bacillus strains showed evidence of lipolytic activity at 10 C in this examination, while only three strains actually grew at 10 C in the temperature study (Table III). The difference in methods and growth media are factors in this apparent difference, but it is also more likely that, although some metabolic activity occurred, such as the limited production of extracellular lipase enzyme, overall activity at 10 C was insufficient for cellular growth and reproduction such as that which would be required to produce positive results in the temperature growth study. These data are encouraging, however, in that it could be possible with certain nutrient selection, or increased oxygen, to culture these organisms more robustly at 10 C in a lipid environment.

Myriad uses are envisioned for the products of the present invention. The claimed bacteria and/or the enzymes produced thereby can be used in a number of wastewater treatment or plumbing system applications, including treatment of municipal or residential wastewater, treatment of on site sewage disposal systems, such as septic systems, and cesspools, pretreatment and/or treatment of food processing wastewater, and as drain openers or cleaners for waste lines, sinks, tubs or other plumbing systems. The claimed bacteria or enzymes may also be used in agricultural applications, such as for Direct Fed Microbials, which can be added to livestock feed to increase food digestion and utilization, as silage innoculants and to treat livestock manure. The claimed bacteria or enzymes may be useful as detergents in a variety of applications, and the enzymes could be used in spot removers or for food processing applications.

The bacteria of the present invention can also provide an original gene pool for recombinant bacteria applications and further recombinant DNA work. It is probable, given the current knowledge and sophistication of recombinant genetics, that the gene(s) controlling lipase production from one or all of these bacteria could be inserted into the DNA of other species to deliver the capability to the receiving species. If the receiving species is a food for humans or livestock, it could become the carrier for the characteristic to enhance food processing and utilization.

The lipase enzymes recovered from the fermentation of such Bacillus bacteria are expected to have a variety of uses, including in food preparation and processing, or in detergents or cleaners to degrade fats and greases on clothing, linens and on surfaces in kitchens and other food preparation areas, and in sinks, drain lines and grease traps.

Although the invention has been described in detail and with references to applications in several areas known to utilize beneficial bacteria for process improvement and greater efficiencies, it is acknowledged that it will be apparent to one skilled in the art that modifications, changes, and formulations with other biological or chemical ingredients can be made without departing from the basic spirit of the present invention. Accordingly, it will be appreciated by those skilled in the art that within the scope of the appended claims, the invention may be practiced other than has been specifically described herein. Hence, the attached claims are intended to cover the invention embodied in the claims and substantial equivalents thereto.

What is claimed is:

1. An isolated microorganism of the strain Bacillus ATCC 202138.

2. The microorganism of claim 1, determined to be species *B. subtilis* by the Fatty Acid Methyl Ester Analysis method using Trypticase Soy Broth Agar version 3.9 at 28.0 C of the database of Microcheck, Inc. of Northfield, Vt.

3. A combination comprising the microorganism of claim 1 and one or more other microorganisms.

4. A method of treating wastewater comprising the step of adding to the wastewater the combination of claim 3.

5. A method of treating plumbing system components comprising the step of introducing into the components the combination of claim 4.

6. A method of treating animal feed comprising the step of adding the combination of claim 3 to the feed.

7. A method of treating wastewater comprising the step of adding to the wastewater the microorganism of claim 1.

8. A method of treating plumbing system components comprising the step of introducing into the components the microorganism of claim 1.

9. A method of treating animal feed comprising the step of adding the microorganism of claim 1 to the feed.

* * * * *

UNITED STATES PATENT AND TRADEMARK OFFICE
CERTIFICATE OF CORRECTION

PATENT NO. : 6,162,634  
DATED : December 19, 2000  
INVENTOR(S) : David Lawler et al.

Page 1 of 1

It is certified that error appears in the above-identified patent and that said Letters Patent is hereby corrected as shown below:

Title page,
Item [54], add -- Novel -- before "Enzyme-Producing".

Claim 5,
Line 3, please change "claim 4" to -- claim 3 --.

Signed and Sealed this

Twentieth Day of November, 2001

Attest:

NICHOLAS P. GODICI
Attesting Officer     Acting Director of the United States Patent and Trademark Office